United States Patent [19]

Hendrickson

[11] Patent Number: 4,836,939

[45] Date of Patent: Jun. 6, 1989

[54] STABLE EXPANDABLE FOAM & CONCENTRATE & METHOD

[75] Inventor: Constance Hendrickson, Irving, Tex.

[73] Assignee: Rockwood Systems Corporation, Lancaster, Tex.

[21] Appl. No.: 188,095

[22] Filed: Apr. 27, 1988

Related U.S. Application Data

[63] Continuation of Ser. No. 889,272, Jul. 25, 1986, abandoned.

[51] Int. Cl.$^4$ .................. C09K 21/00; F42B 33/00; B01J 13/00; A62D 1/08
[52] U.S. Cl. .......................... 252/3; 102/303; 86/50; 252/8.05; 252/307; 252/382; 252/607; 252/610; 252/350; 252/351; 169/46
[58] Field of Search .............. 252/2, 3, 307, 382, 252/8.5 C, 8.05, 607, 610, 350, 351; 86/50; 169/46, 47, 68, DIG. 2; 424/43; 102/303; 261/DIG. 26

[56] References Cited

U.S. PATENT DOCUMENTS

| | | | |
|---|---|---|---|
| 2,469,914 | 5/1949 | Bridgeman | 252/307 |
| 2,875,555 | 3/1959 | Thiegs | 252/307 |
| 3,394,768 | 7/1968 | Chocola et al. | 252/307 |
| 3,422,011 | 1/1969 | Jackovitz et al. | 252/3 |
| 3,579,446 | 5/1971 | Kroke et al. | 252/3 |
| 3,634,233 | 1/1972 | Hiltz | 252/3 |
| 3,681,253 | 8/1972 | Arthur et al. | 252/307 |
| 3,713,404 | 1/1973 | Lavo et al. | 252/307 |
| 3,956,138 | 5/1976 | Crockett | 252/8.05 |
| 4,342,665 | 8/1982 | Itoh et al. | 252/316 |
| 4,442,018 | 4/1984 | Rand | 252/3 |
| 4,541,947 | 9/1985 | Clark et al. | 252/307 |
| 4,589,341 | 5/1986 | Clark et al. | 252/3 |

FOREIGN PATENT DOCUMENTS

| | | | |
|---|---|---|---|
| 49-31234 | 8/1974 | Japan | 252/3 |
| 0763591 | 9/1980 | U.S.S.R. | 252/3 |

*Primary Examiner*—Howard J. Locker
*Attorney, Agent, or Firm*—Beehler, Pavitt, Siegemund, Jagger, Martella & Dawes

[57] ABSTRACT

A stable aqueous foam concentrate for use in the generation of a stable aqueous foam having an expansion ratio of between 10:1 to as high as 1000:1 or more includes an anionic surfactant material of a chain length of between C12 to C14, a glycol or mixtures thereof, a fatty alcohol of between C12 and C14 chain length and a copolymer of maleic anhydride. The components, other than the polymer are mixed to form a micellar structure and the polyer is then added to react with at least one of the components of at least some of the micelles. Upon foam formation, the polymer which is covalently bound operates to reduce the water drainage rate to increase the foam stability, the foam being biodegradable.

11 Claims, No Drawings

STABLE EXPANDABLE FOAM & CONCENTRATE & METHOD

This is a continuation of co-pending application Ser. No. 889,272 filed on July 25, 1986 (now abandoned).

FIELD OF INVENTION

The present invention relates to aqueous foam systems and more particularly to an improved stable expandable aqueous foam system, concentrate and an improved method for making and using such a foam concentrate, and a material which is capable of relatively high expansion.

BACKGROUND OF THE INVENTION

Expandable aqueous foams are known and have been used for various purposes such as fire fighting foams, and the like. In U.S. Pat. No. 4,541,947, assigned to the same assignee, the use of high expansion foams for crowd control and other uses is described. In U.S. Pat. Application Ser. No. 744,511, filed June 13, 1985, now U.S Pat. No. 4,589,341, granted on May 20,1986 and assigned to the same assignee, the use of high expansion foams for blast control and suppression of blast effects is disclosed. In U.S. Pat. Application Ser. No. 777,921, filed Sept. 19, 1985, refiled on Mar. 27, 1987 as continuation application Ser. No. 030,893 (now abandoned) and assigned to the same assignee, the use of such foams as system to encapsulate toxic and other materials is disclosed. In U.S. Pat. Application Ser. No. 781,248, filed Sept. 27, 1985, (now abandoned) and assigned to the same assignee, the use of such foams as a security system is described.

It is apparent from the above that stable high expansion aqueous foams have special utility in fields well known to date. In U.S. Pat. No. 4,442,018 of Apr. 10, 1984 issued to Peter B. Rand, a high expansion, stable aqueous foam is described which includes a water soluble polymer of the polyacrylic acid type having a molecular weight of about 500,000, a foam stabilizer of dodecyl alcohol, a surfactant, and a solvent, all in water is used as a foam concentrate for use in producing what is said to be an improved stabilized high expansion foam.

U.S. Pat. No. 4,439,329 of March 27, 1984 and issued to Kliner et al also discloses a fire fighting foam which is said to be stable through the use of a oleophilic hydrocarbamyl sulfide terminated oligomer as the surfactant.

The generating equipment for producing such expandable foams is well known and is described in the patents and applications previously identified.

The stability of foams is generally identified in terms of the liquid drainage rate of the foam. In effect this is a measure of the rate at which the liquid water drains from the foam and reflects the density stability of the foam and is a standard frequently used. Typically it is referenced in terms of a percentage by weight for a period of time, e.g., 50% by weight drainage for 30 minutes.

One of the important qualities of a foam concentrate is the storage ability of the foam and the ability of the concentrate to remain properly dispersed during shipment and storage. If there is separation of the component of what is usually a multicomponent mixture, the concentrate may have to be remixed before use. This, of course, presents significant problems at the site of use since it is usually a situation where there is no immediately available mixing equipment and the separated components may not be easily redispersed merely by shaking the concentrate. Even if the materials may be redispersed, this may take time in a circumstance in which time is critical, for example, at the site of a dangerous fire, toxic spill or immediate security problem, see the patents and applications to which reference has already been made.

Another aspect of such foams is the impact which the same may have on the environment. Materials which are not biodegradable may obviously present serious consequences in use and thus might be used only as a last alternative due to environmental problems. This consideration may severly restrict the use of expandable foams where their use is clearly appropriate as the most effective solution to an immediate and perhaps emergency problem. For example, the alcohols used in the foam of the Rand patent tends to reduce the biocompatibility of the foam and foam concentrate there disclosed.

Experience with the Rand type of foam has also brought up some added problems, although that foam and concentrate are said to represent an improvement in terms of stability. More specifically, it is believed that foam stability improvement is achieved in that foam material is reinforced by a polymer which is non-reactive in the sense that the polymer is dispersed and physically rather than chemically associates with the small bubbles of the foam to inhibit water drainage and thus bubble collapse. A physical association in the foam operates for a limited period of time and as the water is freed from the foam, the foam density is reduced as measured by the drainage rate, i.e., the rate at which water liquid is released with the result that the bubbles collapse. In a sense the polymer is a fiber type of element that tends to hold the bubbles together, but the polymer may be relatively insoluble in water and thus the alcohol is used as a cosolvent.

It has also been noted that some of the components of the Rand foam tend to gel when exposed to humidity during manufacture, that is, the polymer and the alcohol cosolvent must be anhydrous or the components tend to form a gel which is difficult to redisperse during mixing of the components. The attempted manufacture of commercial quantities of this prior art foam concentrate from materials as commercially available, i.e., in a non-anhydrous form has indicated that the addition of the polymer tends to produce a concentrate which is non-uniform in composition, i.e., one or more of the components tend to separate out. There have also been mixing and subsequent handling problems and separation. The biocompatibility problem has already been discussed. All in all, the Rand type foam is difficult and expensive to manufacture.

More specifically, the procedure for making the Rand product involves the use of polyacrylic acid said to be used to viscosify aqueous systems in the cosmetics field. The polyacrylic acid polymer is usually dissolved in an alcohol of C2 to C5 in length. These alcohols, especially the C3 and above alcohols are difficult to use if they have absorbed moisture and if the polymer has absorbed moisture. When the polymer is mixed with the alcohol, the result is a gummy mass which is difficult, if not impossible to use. While the polymer may be dried overnight in an oven at 65 degrees C., this is not a practical commercial operation especially if the alcohol also has to be treated, as by flow through a molecular sieve to form an anhydrous alcohol. These materials are also hygroscopic and tend to pick up moisture from the air, also leading to manufacturing problems. It is significant that the Rand concentrate also has a viscosity of about 50 centipoises.

At this relatively high viscosity it is difficult to form a thoroughly mixed prefoam mixture, i.e., the water diluted mixture from which the foam is formed. Normally the prefoam mixture is a dynamic mixing operation in which the concentrate is mixed with water at the generator and then flowed to the bubble forming mechanism, normally some form of screen. With uneven mixing of the prefoam material, there are concentrate rich and concentrate starved sections which tend to produce foams of less than the desired quality and uniformity. While this could be overcome by thoroughly premixing the concentrate to form the prefoam mixture, that is undesirable and not effectively achieved at the site of use.

The above difficulties have severely limited the use of the Rand foam and have effectively prohibited its use in areas other than those mentioned.

More specifically, expandable aqueous foams which are stable and biodegradable offer significant potential as a delivery mechanism for various products such as insecticides, pesticides and the like and other agricultural treatment products. By incorporating such products in a stable expandable foam they may be delivered precisely and in a controlled and defined manner to the site of application without concern that such products will be dissipated over a wide area by the wind. Since the foam includes a surfactant, the plants are wetted easily and the effective ingredient is effectively placed over the entire foliage. This type of delivery system is particularly effective for herbicides where it is desired to control accurately the site of delivery and the application. In effect the foam bun remains in place for some period of time and the effective delivery system tends to reduce the amount of such materials which need to be used since the application is controlled by control of placement of the foam bun. A stable, expandable foam in accordance with the present invention may also be used in certain types of agricultural applications to protect against crop freezing.

Another use of the foam of this invention is as a litter for laboratory and test animals. The practice to date has been to use newspaper or some form of dry litter. The objection is the odor generated by the animal droppings and the difficulty in cage and pen clean-up as well as the general sanitary condition of the cages and animals. The use of a foam of the type here described, which is stable and biodegradable offers several advantages. First, the surfactant, which acts as a detergent, tends to keep the pens and cages clean and is easily rinsed away along with all of the animal waste. Odors are suppressed since the foam remains as a blanket in the cages and prevents or at least inhibits migration of the odor. Further, the general cost is less due to the manual operations involved in prior litter systems.

It is thus an object of the present invention to provide an improved foam concentrate and foam system which is easier to manufacture and which is relatively stable in comparison to prior art foams.

It will be apparent from the detailed description which follows that there are several advantages to the present invention which will become apparent to those skilled in the art.

BRIEF DESCRIPTION OF THE INVENTION

The improved material of this invention is in the form of an aqueous foam concentrate which may be diluted in accordance with known data and procedures to provide a expandable, stable aqueous foam system which is relatively easily biodegraded. The generated foam, which has remarkable stability, may have an expansion ratio of from 10:1 to more than 900:1. The concentrate may be made by the improved method to be discussed, is relatively stable against separation and can be shipped and stored without major problems.

Unlike the prior foams and foam concentrates, the present invention utilizes a reactive polymer whose reaction products increase the solubility of the reaction product in water. The polymeric material is cross-linked within the foam concentrate and with the micellar structures which are substructures within the concentrate and which contain the surfactant which participates in the production of foam. In effect what is accomplished is the formation of a micellar structure in the concentrate in which the polymeric product cross-links with that spherical structure of the micelles to stabilize the resulting foam by effectively providing a backbone. It is known, for example, that surfactants form micelles and that an important property of micelles is solubilization, i.e., the spontaneous dissolving of a substance by reversible interaction with micelles of a surfactant in a solvent to form a thermodynamically stable isotropic solution with reduced thermodynamic activity of the dissolved material.

This type of solubilization is different from hydrotrophy, the dissolution of normally insoluble materials in concentrated solutions of hydrotropes, and from emulsification which refers to dispersion of one liquid phase in another; in solubilization the solublized material (referred to as the solubilizate) is in the same phase as the solubilizing solution.

To better understand the novel foam and foam concentrate of the present invention, an understanding of the methodology of forming the concentrate and the foam may be appropriate.

In general, the present invention involves the use of materials which can be said to have hydrophobic tail elements and materials which can be said to have charged head elements. Micelle formation is known to be dependent upon the order in which the components are admixed and the time of contact or association of the mixed components. The objective of this invention is the formation of a micelle configuration in the preconcentrate which permits the addition of a polymer material which is reactive to the micelles and which essentially bonds the micelles together in the concentrate. Upon foam formation the micelle-polymer bond remains intact except that the the surfactant molecules now reside in the bubble walls rather than in the micelle. The result is a complex but desirable bubble structure in which the the bubble formation is interwoven with polymeric strands changing the wall character of the wall and thus favorably altering the the drainage quality of water from the bubbles to provide foam stability as good as that of the Rand system but without the problems associated with the Rand system.

The method of this invention involves formation of a micelle structure in which some components of the material are in a micelle formation as a preconcentrate. The reactive polymer is then added to the formed micelle preconcentrate with the result that the chemical bonding to the micelles is sufficient to to provide a stable concentrate and a stable foam material. It is believed that the bubble formation involves a unique bubble structure which is to be described in detail.

Micelle formation is related to the type of material used, usually a surfactant type material and other material to be described in which the molecules have hydrophobic tails and spaced charged heads or hydrophilic ends. The procedure for micelle formation, in polar solvents that have two or more hydrogen-bonding centers, is both order dependent and time dependent in that the order in which the components are mixed and the length of time of mixing should be controlled to promote micelle formation.

In the initial mixing there is a random orientation of the materials, followed by a stage in which the components begin to assume an orientation on the basis of hydrophobic (tail-to-tail) and hydrophilic (charge-to-charge) interactions. As the concentrations rise, the critical micelle concentration (CMC) is reached. Finally, the charge heads are solubilized by the water and the insoluble tails are ordered inwardly to form the final micelle structure in which there is a high degree of order and dense packing. The CMC is apparent from the abrupt changes in detergency, surface tension, osmotic pressure, viscosity and conductivity which occur. At this stage the material is referred to as a preconcentrate.

The addition of the polymer to the preconcentrate, having reactive groups which may react with one or more components available from the micelle, tends to result in a stable mixture in which the micelle units are connected to the polymer chain at the reactive sites. The resulting concentrate exhibits good stability and is capable of being used to generate a foam.

As the concentrate is diluted with water and processed to a foam, by equipment itself well known, the polymer-to-surfactant bonds are still in tact although the surfactant now resides in the bubble walls rather than in a micelle. The bubble complex is interwoven with the polymer strands thus changing the wall character and the drainage quality of the foam to provide improved foam stability.

DETAILED DESCRIPTION OF THE INVENTION

The foam of the present invention is a mass of essentially uniform bubbles, to be described, made from a water containing concentrate in which one part of the concentrate may be expanded from 10 to about 1000 parts of foam. Foam generators are available which are capable of producing between 1,250 and 22,000 cubic feet of foam per minute and use water at the rate of 37 gallons per minute at 75 psi to as high as 165 gallons per minute at a pressure of about 100 psi. While the generated foam is generally benign, additives may be included depending upon the use of the foam, as described in the application and patents to which reference has already been made.

In accordance with this invention, it has been discovered that the stability of the resulting foam and the stability of the foam concentrate may be improved, while providing a relatively simple manufacturing procedure through the formation of a micellar structure in a preconcentrate and the subsequent use a polymer which is reactive to components of the formed micelles and which is preferably at least partially water soluble. The reactive polymer is preferably a moderate molecular weight material having reactive groups such as anhydride groups available for reaction. A typical and preferred material is a poly(methyl vinyl ether/maleic anhydride) copolymer having a molecular weight in the range of about 20,00 to 41,000 and available under the trade name Gantrez AN. This material is further characterized by the fact that it is soluble in water amd several organic solvents, including alcohols. It is further characterized by the fact that in the presence of water the anhydride linkage is cleaved to form a highly polar polymeric free acid or the corresponding partial esters. The material is also available as a free acid and as the mono-ester, although the anhydride form is preferred so that there will be reaction with the micelles, as will be described.

In general, the procedure for forming the concentrate in accordance with this invention involves the formation of a preconcentrate and mixing and processing the same so that the desired micelle formation takes place and thereafter adding the polymeric material. Typically the preconcentrate is made by admixing, in water, the appropriate surfactants, preferably anionic surfactants, and an alcohol having the same or similar hydrophobic tail as the surfactant. For example, laurel sulfate (ethoxylated) in the form of the ammonium salt or alkyl ether sulfate in the form of the sodium or ammonium salt is added to water and mixed in. The chain length is typically a straight chain and is in the range of C12 to C14, and mixtures thereof may be used, if desired. Propylene glycol or other glycol such as hexylene glycol or ethylene glycol is then added and mixed into the system. It is preferred that propylene glycol be used.

At this point a fatty alcohol having a length of C12 to C14 is added. This length of chain is used so that the chain length is close to that of the surfactants. The fatty alcohol may be added before the propylene glycol, if desired, but the addition of the fatty alcohol after the addition of the propylene glycol seems to work better. The final step in the formation of the preconcentrate is the addition of lauryl sulfate, as the ammonium salt or alkyl sulfate as the ammonium or sodium salt, again of a chain length in the C12 to C14 range.

It is at this stage that micelle formation and takes place as the concentration of the components reaches the CMC with the result that the micellization is completed with the orientation of the molecules as already described. To the formed micelle material, the preconcentrate, is added the polymer material for the purpose of reaction with a component of the micelle and covalent bonding thereto to form the finished concentrate.

If the polymer is added to the water as the first step, it is believed that the di-acid is formed from the anhydride and none is available for reaction with the components of the micelle. The result is what appears to be an acid solution of the anhydride starting material. If the polymer is added after the ethoxylated lauryl sulfate, there is no micelle formation but the complexes that are formed either precipitate or float depending upon the molecular weight of the polymer. If the polymer is added after the glycol, there may be reaction with the glycol and the formation of a complex which either floats or sinks.

Addition of the polymer before the lauryl sulfate results in the sulfate, or at least a part thereof, being effectively excluded from micelle formation. The result is that the polymer effectively blocks at least a portion of the sulfate from associating in the micelles. Addition of the polymer as the last ingredient, especially where the polymer is reactive with alcohols, ammonia and the other functional groups mentioned, results in a covalent bonding of the polymer to the micelle and some formation of the polymeric acid. Before the addition of the polymer, the pH of the preconcentrate has been observed to be in the range of 5.8 to 6.0 and about 4.5 to 5.0 after polymer addition.

The ethoxylated lauryl sulfate is supplied as a 60% solids solution in water and may be used in amount of 25% to 50% with 33.3% being preferred; the solids content varying from 15% to 30% with about 20% being preferred. All the percentages herein set forth being based on weight. The amount of the glycol may be in the range of 3% to 15% with 7.5% being preferred. The fatty alcohol may be present in the range of from 1.0 to 5.0% with 3.3% being preferred. The lauryl sulfate, supplied as a 30% to 40% solids dissolved in water may be present in the range of from 7.0% to 20% with 13.3% being preferred; the solid content being in the range of from 2.1% to 8.0% with the range of about 4.0% to 5.5% being preferred. The balance is make-up water (added at the start) to bring the final concentrate to 100%. The water content may vary form 40% to 80% by weight.

Using the minimum values above given, the non-water content in the preconcentrate ranges from 21.1% to 21.8% and the water content varies from 78.9% to 78.3%. In the preferred amounts set forth, the water content ranges from 65.23% to 63.9% while the non-water content ranges from 34.77% to 36.1%. In the maximum amounts set forth, the non-water content is in the range of 56% to 58% and the water is present in an amount of 44% to 42%.

On a percentage solids basis the ranges of the various components is as follows:

| Component | Minimum | Maximum | Preferred |
| --- | --- | --- | --- |
| Lauryl sulfate ethoxylated | 15 | 30 | 20 |
| Glycol | 3.0 | 15 | 7.5 |
| Fatty alcohol | 1.0 | 5.0 | 3.3 |
| Lauryl Sulfate | 2.1 | 8.0 | 4–5.5 |

The amount and molecular weight of the polymer added has an effect upon the final product in terms of concentrate and foam. For example, the use of polyacrylic acid polymers of various molecular weights, or copolymers of vinylpyrrolidone and styrene and amines produced no noticeable effect on foam stability. The use of a poly(methyl vinyl ether/maleic anhydride) copolymer of molecular weight at or above 50,000, in an amount by weight of 1% based on total composition resulted in a gel formation in the concentrate which sank to the bottom and the latter material was not useable as a foam generating material. If too much of the lower molecular weight polymer is used, a gel-like material forms which floats to the surface, i.e., at concentration, based on total weight of greater than about 9.0%. The same material up to about a 7.5% concentration operates satisfactorily. In the case of the medium molecular weight material (41,000), the optimum range is between 2.5% and 3.5%, based on the weight of the concentrate. Above about 3.5%, this medium weight material results in a gel which sinks. Overall, the percentage of the medium and lower molecular weight material should be above 2% by weight and less than about 7.5% by weight.

The following data is a comparative data of foams in accordance with this invention and a prior art foam:

|  | Expansion | Drainage at 10 min. |
| --- | --- | --- |
| Control | 900:1 | 18–20% |
| 3.5% of medium molecular weight | 962:1 | 2.5% |
| 7.5% of low molecular weight | 913:1 | 12% |

It should be noted that the preferred concentrate material in accordance with the present invention has a viscosity of about below about 25 centipoises and preferably about 14.0 centipoises and is easily mixed with water to form a prefoam for use in foaming equipment.

The total mixing time for formation of the concentrate may vary from one to twenty-four hours depending upon the amount being mixed. Since the manufacturing procedure, for example for 500 gallon quantities, is essentially a mixing operation, the mixing may be carried out overnight in conventional propeller mixers in the absence of high shear mixing which tends to inhibit micelle formation.

In general, the amount of concentrate used to form the prefoam mix and thus the foam may vary depending upon the expansion ratio. The concentrate of this invention may be used to form foams with an expansion ratio which varies from 10:1 to about 1000:1 or more, depending upon the purpose for which the foam is used. For example, when used for animal cages the ratio at the lower end of the range, 10:1 to 30:1 is appropriate. High expansion foams typically are in the ratio of 150:1 and higher.

As is typical of foams of the type to which this invention relates, the presence of a surfactant causes to the foam to flow and wet the items which it contacts. By formulating the concentrate as described, the resulting foam is quite stable against collapse due to drainage of the water over essentially the entire range of expansion ratios. The stability is believed due to the unique coaction of the polymer material which remains covalently bound to the micelle components which enter into the foam formation.

The foam bubble is believed to include an inner wall in which the tails of the surfactant are oriented inwardly and an out wall in which the tails of the surfactant are oriented outwardly, the center section including the charged heads and water. Drainage occurs as the water gradually flows out of this region causing the bubble to collapse, i.e., the water drainage is along the interior of the bubble wall. The use of a polymer material as herein described appears to result in the bubble wall being interwoven with polymer strands tending to maintain wall segment fixation and markedly retarding drainage and bubble collapse. Since the polymer is covalently coupled to a component which forms the bubble wall, formation of bubbles from the micelles of the concentrate maintains the polymer in association with the surfactant which forms the bubble.

In addition to the foregoing components, the concentrate may include a biocide to inhibit bacterial breakdown of the concentrate by bacterial damage to the surfactant. The biocide may be added as a part of the surfactant and is usually supplied in that form. Effective amounts of biocides are well known in the art. The presence of a biocide operates to assure that damage due to bacterial growth during storage does not adversely affect the concentrate.

It will be apparent from the above detailed description that a much improved foam concentrate, foam and method of making the same has been described. To those skilled in the art of foams and related such products, it will be apparent that various modifications may be made, based on the foregoing description, without departing from the scope of the present invention as set forth in the appended claims.

What is claimed is:

1. An aqueous concentrate composition for production of stable aqueous foam comprising:
   a water carrier,
   a micellar structure dispersed through said water in which the micelles include a surfactant material, a corresponding fatty alcohol and glycol,
   a water soluble reactive polymer initially in anhydride form covalently bonded and cross-linked to at least one component of at least some of the micelles to form a reaction product having a greater solubility in water than said polymer and to provide stability to said concentrate and to improve the drainage of the foam formed by said concentrate, and
   a biocide present in said concentrate in an amount effective to prevent bacterial damage to said surfactant material.

2. An aqueous concentrate as set forth in claim 1 wherein said surfactant material is an anionic surfactant material having a chain length of from C12 to C14 and said fatty alcohol having a chain length of from C12 to C14.

3. An aqueous concentrate as set forth in claim 1 wherein said polymer is a maleic anhydride copolymer having a molecular weight of between above about 20,000 and less than about 50,000 units.

4. An aqueous concentrate as set forth in claim 1 wherein the water content is between 40% and 80% by weight.

5. An aqueous concentrate as set forth in claim 3 wherein the amount of said polymer is between 2% and 7.5% by weight.

6. An aqueous concentrate as set forth in claim 1 wherein the surfactant material is present by weight in an amount of between 17% and 38%, the fatty alcohol being present by weight between 1% and 5%, the glycol being present by weight between 3% and 15%, the polymer being present by weight between 2% and 7.5%, and the balance being water.

7. An aqueous concentrate as set forth in claim 6 wherein said surfactant is selected from the group consisting of ethoxylated lauryl sulfate, the ammonium salt thereof, alkyl ether sulfate and the sodium and ammonium salts thereof, and mixtures thereof; the glycol is selected from the group consisting of propylene glycol, hexylene glycol and ethylene glycol and mixtures thereof, and said fatty alcohol having a chain length of between C12 and C14.

8. An aqueous concentrate as set forth in claim 1 wherein said concentrate has a viscosity below about 25 centipoises.

9. An aqueous concentrate useable in forming a stable aqueous foam comprising:
   water in an amount by weight of between 40% and 80%,
   a glycol material in an amount by weight of between 3% and 15%,
   an anionic surfactant material having a chain length of between $C_{12}$ and $C_{14}$ and present in an amount by weight of between 17% and 38%,
   a fatty alcohol present in an amount by weight of between 1% and 3% and having a chain length of between C12 and C14, and
   a copolymer of maleic anhydride which is soluble in water and reactive with respect to alcohol and water to form an acid and an ester, said polymer having a molecular weight of more than about 20,000 and less than about 50,000 units and being present in an amount by weight of between 2% and 7.5%.

10. An aqueous foam made from the concentrate set forth in any one of the preceding claims 1 to 9 and having an expansion ratio in the range of 10:1 to more than 1000:1.

11. A method of forming an aqueous concentrate for use in forming an aqueous foam, comprising the steps of:
   admixing in water an anionic surfactant followed by the addition of a long chain fatty alcohol having a chain length essentially equal to that of the surfactant and a glycol,
   adding additional surfactant and mixing the formed material for a time sufficient to effect micellization, and
   thereafter adding a water soluble polymer having functional groups reactive with the components of said micelles to effect covalent bonding of the polymer to at least some of said micelles.

* * * * *